United States Patent [19]

Soma et al.

[11] 4,118,368

[45] Oct. 3, 1978

[54] SYNTHETIC POLYMER STABILIZERS

[75] Inventors: Nobuo Soma; Syoji Morimura; Takao Yoshioka; Tomoyuki Kurumada, all of Tokyo, Japan

[73] Assignee: Sankyo Company Limited, Tokyo, Japan

[21] Appl. No.: 739,055

[22] Filed: Nov. 5, 1976

[30] Foreign Application Priority Data

Nov. 11, 1975 [JP] Japan .................... 50-135516

[51] Int. Cl.$^2$ ................ C07D 211/00; C07D 401/12; C08K 5/34
[52] U.S. Cl. ............... 260/45.8 N; 260/45.8 NT; 260/293.63; 260/293.87; 260/293.88
[58] Field of Search ........... 260/45.8 N, 293.63, 260/293.87, 293.88

[56] References Cited

U.S. PATENT DOCUMENTS

| 3,684,765 | 8/1972 | Matsui et al. ............... 260/45.8 N |
| 3,850,877 | 11/1974 | Cook ............................. 260/45.8 N |
| 3,904,581 | 9/1975 | Murayama et al. .......... 260/45.8 NP |
| 3,959,291 | 5/1976 | Cook ............................. 260/293.66 |
| 3,993,470 | 11/1976 | Devaux et al. ............... 71/94 |
| 4,064,102 | 12/1977 | Hillard et al. ................ 260/45.8 NP |

OTHER PUBLICATIONS

Joss et al., J. Org. Chem., vol. 37, No. 12, 1972, pp. 2015–2018.
Rassat et al., Chem. Abs., vol. 70, 1969, 3846m.

*Primary Examiner*—Donald E. Czaja
*Assistant Examiner*—R. A. White
*Attorney, Agent, or Firm*—Toren, McGeady and Stanger

[57] ABSTRACT

Novel derivatives of 4-amino-2,6-dimethylpiperidine have additional methyl or substituted-methyl substituents at positions 2 and 6, and a carboxylate ester substituent at position 4. Positions 1 and 3, and the amino group at position 4, can optionally also be substituted. These derivatives are useful for stabilizing synthetic polymers, especially polyolefins, polyamides and polyurethanes, against photo- and thermal-deterioration, generally in an amount of 0.01 – 5.0% by weight based on the polymer.

9 Claims, No Drawings

SYNTHETIC POLYMER STABILIZERS

BACKGROUND OF THE INVENTION

This invention relates to certain novel substituted piperidine derivatives and to their use as stabilizers for synthetic polymers, and provides processes for their preparation. More specifically, it is concerned with piperidine derivatives of the type having four methyl or substituted methyl groups at positions 2 and 6, and an amino or substituted amino group at position 4.

Substituted piperidine polymer stabilizers of this general type are disclosed in U.S. Pat. Nos. 3,534,048, 3,684,765, 3,705,166 and 3,904,581, Japanese Patent Publication No. 23023/70 (Chemical Abstracts 74, 88439m), French Pat. No. 1 501 917 (Chemical Abstracts 70, 3846m), the Journal of the American Chemical Society 91, 7526 (1969), and the Bulletin de la Societe Chimique de France 1967 (3), 815–817 (Chemical Abstracts 67, 43656u).

SUMMARY OF THE INVENTION

It is an object of the present invention to provide novel piperidine derivatives of this type which have an effective and improved stabilization effect for polymeric materials.

It is a further object of the invention to provide a polymer composition containing an effective stabilizing amount of such a piperidine derivative.

In accordance with these objects, the invention provides piperidine derivatives having the formula

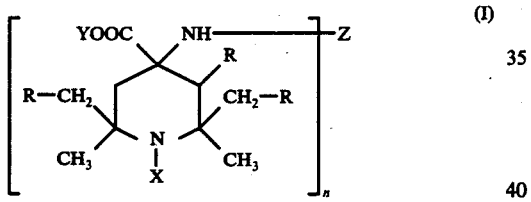

and the acid-addition salts thereof, wherein:
R represents a hydrogen atom, or
  an alkyl group having 1–3 carbon atoms;
X represents a hydrogen atom,
  an oxyl radical,
  an alkyl group having 1–18 carbon atoms,
  an alkenyl group having 3–6 carbon atoms,
  a 2-propynyl group,
  an alkoxyalkyl group having 1–3 carbon atoms in the alkyl moiety and 1–18 carbon atoms in the alkoxy moiety,
  a cyanoalkyl group having 2–3 carbon atoms,
  an 2,3-epoxypropyl group,
  an aliphatic acyl group having 1–12 carbon atoms,
  an aralkyl group optionally substituted in its aryl moiety,
  a group of the formula —CH$_2$CH(R$^1$)OR$^2$ (wherein R$^1$ represents a hydrogen atom, a methyl group or a phenyl group, and R$^2$ represents a hydrogen atom, or an aliphatic, aromatic, araliphatic or alicyclic acyl group having up to 18 carbon atoms), a group of the formula —CH$_2$COOR$^3$, (wherein R$^3$ represents an alkyl group having 1–18 carbon atoms, an alkenyl group having 3–6 carbon atoms, a phenyl group, an aralkyl group having 7–8 carbon atoms, or a cyclohexyl group) or a group of the formula —COOR$^4$ (wherein R$^4$ represents an alkyl group having 1–8 carbon atoms, a benzyl group or a phenyl group);
Y represents an alkyl group having 1–18 carbon atoms,
  an alkenyl group having 3–6 carbon atoms,
  an aralkyl group optionally substituted in its aryl moiety, or
  an alkoxyalkyl group having 2–4 carbon atoms;
n = 1, 2 or 3; and
when n = 1:
Z represents a hydrogen atom,
  an alkyl group having 1–18 carbon atoms,
  an alkenyl group having 3–4 carbon atoms,
  an alkanoyl group having 2–18 carbon atoms,
  an alkenoyl group having 3–5 carbon atoms,
  an aromatic acyl group optionally substituted in its aryl moiety,
  a cinnamoyl group,
  a 3-(3,5-di-t-butyl-4-hydroxyphenyl)propionyl group,
  a phenylacetyl group,
  a phenoxyacetyl group,
  a cyclohexanecarbonyl group,
  an aralkyl group optionally substituted in its aryl moiety,
  a group of formula —CH$_2$CH$_2$OR$^5$ (wherein R$^5$ represents a hydrogen atom, or an aliphatic, aromatic, araliphatic or alicyclic acyl group having up to 18 carbon atoms),
  a group of the formula —SO$_2$R$^6$ (wherein R$^6$ represents an alkyl group having 1–3 carbon atoms, a phenyl group or a tolyl group),
  a group of the formula —COOR$^7$ (wherein R$^7$ represents an alkyl group having 1–8 carbon atoms or a benzyl group),
  a group of the formula —CONR$^8$R$^9$ (wherein R$^8$ represents a hydrogen atom or an alkyl group having 1–4 carbon atoms, and R$^9$ represents a hydrogen atom, an alkyl group having 1–18 carbon atoms, a phenyl group which may optionally be substituted, a naphthyl group, a benzyl group or a cyclohexyl group; or R$^8$ and R$^9$ jointly represent an alkylene group having 4–6 carbon atoms), or
  a group of the formula —CSNHR$^{10}$ (wherein R$^{10}$ represents an alkyl group having 1–4 carbon atoms or a phenyl group);
when n = 2:
Z represents an alkylene group having 1–10 carbon atoms,
  a 2-butenylene group,
  an m- or p- xylylene group,
  a carbonyl group
  a sulfinyl group,
  a sulfonyl group,
  an oxalyl group,
  a group of the formula —CO—R$^{11}$—CO— (wherein R$^{11}$ represents an alkylene group having 1–10 carbon atoms which may optionally be interrupted by a sulfur atom; an alkenylene group having 2–4 carbon atoms; an arylene group having 6 or 10 carbon atoms in its aryl moiety; or a cyclohexylene group), or
  a group of the formula —CONH—R$^{12}$—NHCO— [wherein R$^{12}$ represents an alkylene group having 2–8 carbon atoms; a phenylene group; a tolylene group; a naphthylene group; a xylylene group; a group of the formula

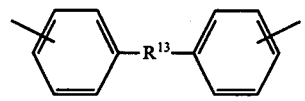

(wherein $R^{13}$ represents an oxygen atom or a methylene group), or a group of the formula

(wherein $R^{14}$ represents a hydrogen atom or a methyl group)];
when $n = 3$:
Z represents a group of the formula

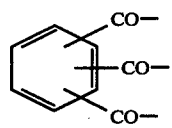

a group of the formula

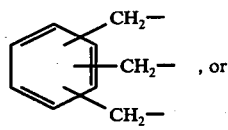

a group of the formula

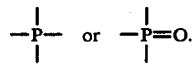

It has been discovered that the novel piperidine derivatives of formula (I) or mixtures thereof and/or acid addition salts thereof can effectively stabilize a wide range of polymers against photo- and thermal- deterioration and are particularly effective for the stabilization of olefin polymers, polyamides and polyurethanes.

In formula (I), when R represents an alkyl group having 1–3 carbon atoms it may be methyl, ethyl, n-propyl or isopropyl, and it is preferably methyl.

When X represents an alkyl group having 1–18 carbon atoms, it may be, for example, methyl, ethyl, n-propyl, n-butyl, n-hexyl, octyl, decyl, hexadecyl or octadecyl, and it is preferably a group having 1–4 carbon atoms, most preferably methyl.

When X represents an alkenyl group having 3–6 carbon atoms, it may be, for example, allyl, 2-butenyl or 2-hexenyl, and it is preferably one having 3 or 4 carbon atoms, most preferably allyl.

When X represents an alkoxyalkyl group having 1–3 carbon atoms in its alkyl moiety and 1–18 carbon atoms in its alkoxy moiety, it may be, for example, methoxymethyl, ethoxymethyl, 2-methoxyethyl, 2-ethoxyethyl, 2-n-butoxyethyl, 2-octyloxyethyl, 2-decyloxyethyl, 2-hexadecyloxyethyl, 2-octadecyloxyethyl, 3-n-butoxypropyl or 2-ethoxypropyl, and it is preferably an alkoxyethyl group having 1–18 carbon atoms in its alkoxy moiety.

When X represents a cyanoalkyl group having 2 or 3 carbon atoms, it may suitably be cyanomethyl or 2-cyanoethyl.

When X represents an aliphatic acyl group having 1–12 carbon atoms, it may be saturated or unsaturated, for example formyl, acetyl, propionyl, butyryl, octanoyl, lauroyl, acryloyl or crotonoyl, and it is preferably an alkanoyl group having 2–4 carbon atoms or an alkenoyl group having 3 or 4 carbon atoms, most preferably acetyl, acryloyl or crotonoyl.

When X represents an aralkyl group optionally substituted in its aryl moiety, it may be, for example, a phenethyl group, or a benzyl group optionally substituted in its phenyl moiety with up to three substituents (which may be the same or different, but preferably with only one substituent) selected from chlorine, $C_{1-4}$ alkyl or $C_{1-8}$ (preferably $C_{1-4}$) alkoxy, for example benzyl, o-, m- or p-chlorobenzyl, o-, m- or p-methylbenzyl, p-isopropylbenzyl, p-t-butylbenzyl, p-methoxybenzyl, p-n-butoxybenzyl or p-octyloxybenzyl. It is preferably benzyl.

When X represents a group of the formula $-CH_2CH(R^1)OR^2$ wherein $R^2$ is an aliphatic, aromatic, araliphatic or alicyclic acyl group, this acyl group may be represented by the formula $-COR^{15}$. In this, $R^{15}$ may suitably be an alkyl group having 1–17 carbon atoms, e.g. methyl, ethyl, n-propyl, isopropyl, n-butyl, heptyl, 1-ethylpentyl, nonyl, undecyl, tridecyl, pentadecyl or heptadecyl; an alkenyl group having 2–4 carbon atoms, e.g. vinyl, 1-propenyl, isopropenyl, 2-methyl-1-propenyl or 1-butenyl; a phenyl group which may optionally be substituted with up to three substituents (which may be the same or different, but preferably with only one substituent) selected from chlorine, $C_{1-4}$ alkyl, $C_{1-8}$ (preferably $C_{1-4}$) alkoxy or hydroxy, e.g. phenyl, o-, m- or p-methylphenyl, p-isopropylphenyl, p-t-butylphenyl, o-, m- or p-chlorophenyl, 2,4-dichlorophenyl, o-, m- or p-methoxyphenyl, p-ethoxyphenyl, p-n-butoxyphenyl, p-octyloxyphenyl, 3,4,5-trimethoxyphenyl, o-hydroxyphenyl or 3,5-di-t-butyl-4-hydroxyphenyl; an aralkyl group having 7 or 8 carbon atoms and optionally substituted with up to three substituents in its aryl moiety (said substituents being the same or different, but preferably with only one substituent) selected from chlorine, $C_{1-4}$ alkyl, $C_{1-8}$ (preferably $C_{1-4}$) alkoxy or hydroxy, e.g. benzyl, phenethyl, p-methylbenzyl, p-chlorobenzyl, p-methoxybenzyl or 3,5-di-t-butyl-4-hydroxyphenethyl; a styryl group; or a cyclohexyl group. Preferably X is a group of the formula $-CH_2CH_2OR^{16}$, wherein $R^{16}$ represents a hydrogen atom, an alkanoyl group having 2–18 carbon atoms, or a benzoyl group.

When X represents a group of the formula $-CH_2COOR^3$, $R^3$ can be an alkyl group having 1–18 carbon atoms (e.g. methyl, ethyl, n-propyl, isopropyl, n-butyl, isobutyl, t-butyl, isopentyl, octyl, dodecyl or octadecyl), an alkenyl group having 3–6 carbon atoms (e.g. allyl, 2-butenyl or 2-hexenyl), a phenyl group, an aralkyl group having 7 or 8 carbon atoms (e.g. benzyl or phenethyl), or a cyclohexyl group. Preferably, $R^3$ is an alkyl group having 1–18 carbon atoms, and most preferably one having 1–4 carbon atoms.

When X represents a group of the formula $-COOR^4$, $R^4$ can be an alkyl group having 1–8 carbon atoms (e.g. methyl, ethyl, isobutyl or octyl), a benzyl group, or a phenyl group. $R^4$ is preferably an alkyl group having 1–4 carbon atoms.

When Y represents an alkyl group having 1–18 carbon atoms, it may be, for example, methyl, ethyl, n-propyl, n-butyl, n-hexyl, octyl, decyl, hexadecyl or octadecyl. Preferably, it is one having 1–8 carbon atoms, and most preferably it is methyl or ethyl.

When Y represents an alkenyl group having 3–6 carbon atoms, it may be, for example, allyl, 2-butenyl or 2-hexenyl. It is preferably one having 3 or 4 carbon atoms, most preferably allyl.

When Y represents an aralkyl group optionally substituted in its aryl moiety, it may be, for example, a phenethyl group, or a benzyl group the phenyl moiety of which may optionally be substituted with up to three substituents (said substituents being the same or different, but preferably with only one substituent) selected from chlorine, $C_{1-4}$ alkyl or $C_{1-8}$ (preferably $C_{1-4}$) alkoxy, e.g. benzyl, o-, m- or p-chlorobenzyl, o-, m- or p-methylbenzyl, p-isopropylbenzyl, p-t-butylbenzyl, p-methoxybenzyl, p-n-butoxybenzyl or p-octyloxybenzyl. It is preferably benzyl.

When Y represents an alkoxyalkyl group having a total of 2–4 carbon atoms, it may be, for example, methoxymethyl, ethoxymethyl, 2-methoxyethyl, 2-ethoxyethyl or 3-methoxypropyl. It is preferably one having a total of 3 or 4 carbon atoms.

The meaning of Z in formula (I) depends on whether the integer $n$ is 1, 2 or 3.

When $n$ is 1:

When Z represents an alkyl group having 1–18 carbon atoms, it may be, for example, methyl, ethyl, n-propyl, n-butyl, n-hexyl, octyl, decyl, hexadecyl or octadecyl; and it is preferably one having 1–8 carbon atoms.

When Z represents an alkenyl group having 3 or 4 carbon atoms, it may be, for example, allyl or 2-butenyl.

When Z represents an alkanoyl group having 2–18 carbon atoms, or an alkenoyl group having 3–5 carbon atoms, it may be, for example, acetyl, propionyl, butyryl, valeryl, pivaloyl, hexanoyl, octanoyl, 2-ethylhexanoyl, lauroyl, palmitoyl, stearoyl, acryloyl, crotonoyl, methacryloyl or $\beta,\beta$-dimethylacryloyl; and it is preferably an alkanoyl group having 2–8 carbon atoms or an alkenoyl group having 3 or 4 carbon atoms.

When Z represents an aromatic acyl group optionally substituted in its aryl moiety, it may suitably be a benzoyl group optionally having up to three substituents (said substituents being the same or different, but preferably with only one substituent) selected from chlorine, $C_{1-4}$ alkyl, $C_{1-8}$ (preferably $C_{1-4}$) alkoxy or hydroxy, e.g. benzoyl, o-, m- or p-chlorobenzoyl, 2,4-dichlorobenzoyl, o-, m- or p-methylbenzoyl, p-isopropylbenzoyl, p-t-butylbenzoyl, o-, m- or p-methoxybenzoyl, p-ethoxybenzoyl, p-n-butoxybenzoyl, p-octyloxybenzoyl, 3,4,5-trimethoxybenzoyl, salicyloyl or 3,5-di-t-butyl-4-hydroxybenzoyl. Alternatively, it may be an $\alpha$- or $\beta$-naphthoyl group, or an $\alpha$- or $\beta$-anthraquinoniloyl group. It is preferably benzoyl.

When Z represents an aralkyl group optionally substituted in its aryl moiety, it may be, for example, a phenethyl group, or a benzyl group optionally substituted in its phenyl moiety with up to three substituents (said substituents being the same or different, but preferably with only one substituent) selected from chlorine, $C_{1-4}$ alkyl or $C_{1-8}$ (preferably $C_{1-4}$) alkoxy, e.g. benzyl, o-, m- or p-chlorobenzyl, o-, m- or p-methylbenzyl, p-isopropylbenzyl, p-t-butylbenzyl, p-methoxybenzyl, p-n-butoxybenzyl or p-octyloxybenzyl. It is preferably benzyl.

When Z represents a group of the formula $-CH_2CH_2OR^5$ and $R^5$ is an aliphatic, aromatic, araliphatic or alicyclic acyl group, said acyl group may be represented by the formula $-COR^{18}$. In this, $R^{18}$ may suitably be an alkyl group having 1–17 carbon atoms (e.g. methyl, ethyl, n-propyl, isopropyl, n-butyl, heptyl, 1-ethylpentyl, nonyl, undecyl, tridecyl, pentadecyl or heptadecyl); an alkenyl group having 2–4 carbon atoms (e.g. vinyl, 1-propenyl, isopropenyl, 2-methyl-1-propenyl or 1-butenyl); a phenyl group which may optionally be substituted with up to three substituents (said substituents being the same or different, but preferably with only one substituent) selected from chlorine, $C_{1-4}$ alkyl, $C_{1-8}$ (preferably $C_{1-4}$) alkoxy or hydroxy (e.g. phenyl, o-, m- or p-chlorophenyl, 2,4-dichlorophenyl, o-, m- or p-methylphenyl, p-isopropylphenyl, p-t-butylphenyl, o-, m- or p-methoxyphenyl, p-ethoxyphenyl, p-n-butoxyphenyl, p-octyloxyphenyl, 3,4,5-trimethoxyphenyl, o-hydroxyphenyl or 3,5-di-t-butyl-4-hydroxyphenyl); an aralkyl group having 7 or 8 carbon atoms and which may optionally be substituted with up to three substituents in its aryl moiety (said substituents being the same or different, but preferably with only one substituent) selected from chlorine, $C_{1-4}$ alkyl, $C_{1-8}$ (preferably $C_{1-4}$) alkoxy or hydroxy (e.g. benzyl, phenethyl, p-methylbenzyl, p-chlorobenzyl, p-methoxybenzyl or 3,5-di-t-butyl-4-hydroxyphenethyl); a styryl group; or a cyclohexyl group. Preferably, Z is a group of the formula $-CH_2CH_2OR^{19}$, wherein $R^{19}$ represents a hydrogen atom, an alkanoyl group having 2–18 carbon atoms or a benzoyl group.

When Z represents a group of the formula $-SO_2R^6$, $R^6$ can be an alkyl group having 1–3 carbon atoms (e.g. methyl, ethyl or n-propyl), a phenyl group, or an o-, m- or p-tolyl group. Preferably, Z is a phenylsulfonyl or p-tolylsulfonyl group.

When Z represents a group of the formula $-COOR^7$, $R^7$ can be an alkyl group having 1–8 carbon atoms (e.g. methyl, ethyl, n-propyl, isopropyl, n-butyl, isobutyl, t-butyl, isopentyl or octyl), or a benzyl group. Preferably, $R^7$ is an alkyl group having 2 or 3 carbon atoms or a benzyl group.

When Z represents a group of the formula $-CONR^8R^9$, $R^8$ can be a hydrogen atom or an alkyl group having 1–4 carbon atoms (e.g. methyl, ethyl, n-propyl or n-butyl); and $R^9$ can be a hydrogen atom, an alkyl group having 1–18 carbon atoms (e.g. methyl, ethyl, n-propyl, n-butyl, n-hexyl, octyl, decyl, hexadecyl or octadecyl), a phenyl group which may optionally be substituted with up to three substituents (said substituents being the same or different, but preferably with only one substituent) selected from chlorine or $C_{1-4}$ alkyl (e.g. phenyl, o-, m- or p-chlorophenyl, o-, m- or p-methylphenyl, p-isopropylphenyl, p-n-butylphenyl or p-t-butylphenyl), an $\alpha$- or $\beta$-naphthyl group, a benzyl group, or a cyclohexyl group. Alternatively, $R^8$ and $R^9$ can jointly represent an alkylene group having 4–6 carbon atoms, e.g. tetramethylene, pentamethylene or hexamethylene. Preferably, $R^8$ is a hydrogen atom; and $R^9$ is preferably an alkyl group having 1–4 carbon atoms, a phenyl group or a p-tolyl group.

When Z represents a group of the formula $-CSNHR^{10}$, $R^{10}$ can be an alkyl group having 1–4 carbon atoms (e.g. methyl, ethyl, n-propyl or n-butyl), or a phenyl group.

When $n$ is 2:

When Z represents an alkylene group having 1–10 carbon atoms, it may be, for example, methylene, ethylene, propylene, trimethylene, tetramethylene, hexamethylene, octamethylene or decamethylene; and it is preferably one having 2–6 carbon atoms.

When Z represents a group of the formula —CO—R$^{11}$—CO—, R$^{11}$ can be an alkylene group having 1–10 carbon atoms and optionally interrupted by a sulfur atom (e.g. methylene, ethylene, propylene, trimethylene, tetramethylene, hexamethylene, octamethylene, decamethylene or 3-thiapentamethylene), an alkenylene group having 2–4 carbon atoms [e.g. vinylene, 2-butenylene or —CH$_2$—C(=CH$_2$)—], an arylene group having 6 or 10 carbon atoms in its aryl moiety (e.g. o-, m- or p-phenylene or 1,5-naphthylene), or a cyclohexylene group (e.g. 1,4-cyclohexylene). Preferably, R$^{11}$ is an alkylene group having 2–8 carbon atoms, an alkenylene group having 2 or 3 carbon atoms, an m- or p-phenylene group, a 1,5-naphthylene group or a 1,4-cyclohexylene group.

When Z represents a group of the formula —CONH—R$^{12}$—NHCO—, R$^{12}$ can be an alkylene group having 2–8 carbon atoms (e.g. ethylene, propylene, trimethylene, tetramethylene, hexamethylene or octamethylene), a phenylene group which may optionally be methyl-substituted (e.g. o-, m- or p-phenylene, 2,4-tolylene or 2,5-tolylene), a naphthylene group (e.g. 1,5-naphthylene), a xylylene group (e.g. m- or p-xylylene), a group of the formula

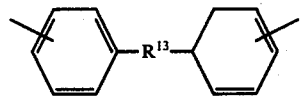

wherein R$^{13}$ represents an oxygen atom or a methylene group (e.g. oxydi-p-phenylene or methylene-di-p-phenylene), or a group of the formula

wherein R$^{14}$ represents a hydrogen atom or a methyl group (e.g. p,p'-diphenylene or 3,3'-dimethyl-4,4'-diphenylene). Preferably, R$^{12}$ is a hexamethylene, 2,4-tolylene, 1,5-naphthylene, m- or p-xylylene, or methylenedi-p-phenylene group.

When n is 3:
When Z is a group of the formula:

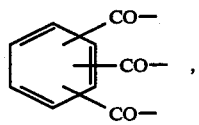

it may suitably be one of

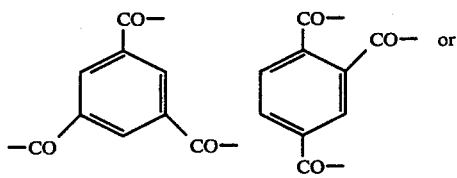

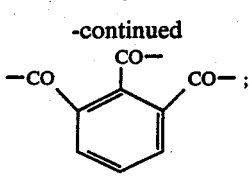

and it is preferably

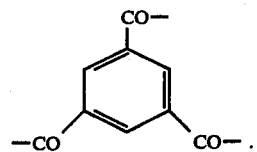

When X is a group of the formula:

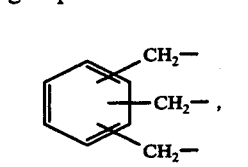

it may suitably be one of

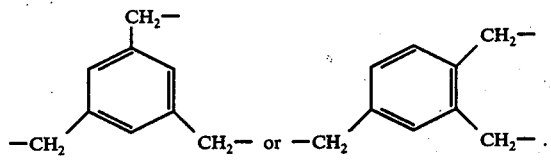

The piperidine derivatives of above formula (I) can exist in the form of various stereoisomers. All of the individual stereoisomers, as well as mixtures thereof, are included within the scope of the invention.

The acid-addition salts of the piperidine derivatives of formula (I) are also included within the scope of the invention. These may be, for example, salts of inorganic acids such as sulfuric, hydrochloric or phosphoric acid; salts of organic carboxylic acids, such as formic, acetic, valeric, stearic, oxalic, adipic, sebacic, maleic, benzoic, p-t-butylbenzoic, 3,5-di-t-butyl-4-hydroxybenzoic, salicylic or terephthalic acid; of sulfonic acids such as methanesulfonic or p-toluenesulfonic acid; or of organic phosphonic acids such as phenylphosphonic acid.

A preferred class of compounds of the invention as those wherein:
R represents a hydrogen atom or a methyl group;
X represents a hydrogen atom, an alkyl group having 1–4 carbon atoms, an allyl group, an alkanoyl group having 2–4 carbon atoms, an alkenoyl group having 3 or 4 carbon atoms, a 2,3-epoxypropyl group, a benzyl group, or a group of the formula —CH$_2$CH$_2$OR$^{16}$ (wherein R$^{16}$ represents a hydrogen atom, an alkanoyl group having 2–18 carbon atoms or a benzoyl group);
Y represents an alkyl group having 1–8 carbon atoms, an allyl group, a benzyl group, or an alkoxyalkyl group having 3 or 4 carbon atoms;
n = 1 or 2; and
when n = 1:
Z represents an alkyl group having 1–8 carbon atoms, an alkanoyl group having 2–18 carbon atoms, an alkenoyl group having 3 or 4 carbon atoms, a benzoyl group, a benzyl group, a phenylsulfonyl group, a p-tolylsulfonyl group, a methylcarbamoyl group, or a phenylcarbamoyl group optionally substituted in its phenyl moiety with a chlorine atom or with an alkyl group having 1–4 carbon atoms;

when $n = 2$:

Z represents an alkylene group having 2–6 carbon atoms, a xylylene group, a group of the formula —CO—$R^{21}$—CO— (wherein $R^{21}$ represents an alkylene group having 2–8 carbon atoms, an alkenylene group having 2 or 3 carbon atoms, a m- or p- phenylene group, a 1,5-naphthylene group or a 1,4-cyclohexylene group), or a group of the formula —CONH—$R^{22}$—NHCO— (wherein $R^{22}$ represents a hexamethylene group, a 2,4-tolylene group, a 1,5-naphthylene group, a m- or p- xylylene group, or a methylenedi-p-phenylene group).

The most highly preferred class of compounds of the invention are those wherein:

R represents a hydrogen atom;

X represents a hydrogen atom, a methyl group, an allyl group, an acetyl group, an acryloyl group, a crotonoyl group, a 2,3-epoxypropyl group, a benzyl group, or a group of the formula —CH$_2$CH$_2$O$R^{16}$ (wherein $R^{16}$ represents a hydrogen atom, an alkanoyl group having 2–18 carbon atoms or a benzoyl group);

Y represents a methyl group, an ethyl group or an allyl group;

$n = 1$ or 2; and when $n = 1$:

Z represents an alkanoyl group having 2–8 carbon atoms, an alkenoyl group having 3 or 4 carbon atoms, a benzoyl group, a methylcarbamoyl group or a phenylcarbamoyl group;

when $n = 2$:

Z represents a group of the formula —CO—$R^{23}$—CO— (wherein $R^{23}$ represents an alkylene group having 2–8 carbon atoms or a p-phenylene group).

The preferred acid-addition salts of these most highly preferred compounds are those formed with carboxylic acids.

The following is a non-limiting list of individual piperidine derivatives of formula (I). The numbers appended to the compounds in this list will be used to identify them hereinafter in the Examples.

1. 4-amino-4-methoxycarbonyl-2,2,6,6-tetramethylpiperidine
2. 4-amino-4-ethoxycarbonyl-2,2,6,6-tetramethylpiperidine
3. 4-amino-4-octyloxycarbonyl-2,2,6,6-tetramethylpiperidine
4. 4-amino-4-octadecyloxycarbonyl-2,2,6,6-tetramethylpiperidine
5. 4-amino-4-benzyloxycarbonyl-2,2,6,6-tetramethylpiperidine
6. 4-methylamino-4-methoxycarbonyl-2,2,6,6-tetramethylpiperidine
7. 4-octylamino-4-octyloxycarbonyl-2,2,6,6-tetramethylpiperidine
8. 4-benzylamino-4-benzyloxycarbonyl-2,2,6,6-tetramethylpiperidine
9. 4-acetamido-4-ethoxycarbonyl-2,2,6,6-tetramethylpiperidine
10. 4-acetamido-4-octadecyloxycarbonyl-2,2,6,6-tetramethylpiperidine
11. 4-acetamido-4-allyloxycarbonyl-2,2,6,6-tetramethylpiperidine
12. 4-acetamido-4-benzyloxycarbonyl-2,2,6,6-tetramethylpiperidine
13. 4-acetamido-4-(p-methoxybenzyloxycarbonyl)-2,2,6,6-tetramethylpiperidine
14. 4-n-valeramido-4-methoxycarbonyl-2,2,6,6-tetramethylpiperidine
15. 4-stearamido-4-methoxycarbonyl-2,2,6,6-tetramethylpiperidine
16. 4-stearamido-4-octadecyloxycarbonyl-2,2,6,6-tetramethylpiperidine
17. 4-crotonamido-4-methoxycarbonyl-2,2,6,6-tetramethylpiperidine
18. 4-benzamido-4-methoxycarbonyl-2,2,6,6-tetramethylpiperidine
19. 4-benzamido-4-ethoxycarbonyl-2,2,6,6-tetramethylpiperidine
20. 4-benzamido-4-allyloxycarbonyl-2,2,6,6-tetramethylpiperidine
21. 4-benzamido-4-benzyloxycarbonyl-2,2,6,6-tetramethylpiperidine
22. 4-benzamido-4-(p-chlorobenzyloxycarbonyl)-2,2,6,6-tetramethylpiperidine
23. 4-benzamido-4-(p-methylbenzyloxycarbonyl)-2,2,6,6-tetramethylpiperidine
24. 4-(p-t-butylbenzamido)-4-methoxycarbonyl-2,2,6,6-tetramethylpiperidine
25. 4-(p-t-butylbenzamido)-4-phenethyloxycarbonyl-2,2,6,6-tetramethylpiperidine
26. 4-(p-methoxybenzamido)-4-ethoxycarbonyl-2,2,6,6-tetramethylpiperidine
27. 4-(α-naphthamido)-4-methoxycarbonyl-2,2,6,6-tetramethylpiperidine
28. 4-[β-(3,5-di-t-butyl-4-hydroxyphenyl)propionamido]-4-methoxycarbonyl-2,2,6,6-tetramethylpiperidine
29. 4-cinnamamido-4-octyloxycarbonyl-2,2,6,6-tetramethylpiperidine
30. 4-methanesulfonamido-4-methoxycarbonyl-2,2,6,6-tetramethylpiperidine
31. 4-(p-toluenesulfonamido)-4-methoxycarbonyl-2,2,6,6-tetramethylpiperidine
32. 4-(3-methylureido)-4-methoxycarbonyl-2,2,6,6-tetramethylpiperidine
33. 4-(3-ethylureido)-4-hexadecyloxycarbonyl-2,2,6,6-tetramethylpiperidine
34. 4-(3-phenylureido)-4-methoxycarbonyl-2,2,6,6-tetramethylpiperidine
35. 4-[3-(m-chlorophenylureido)]-4-methoxycarbonyl-2,2,6,6-tetramethylpiperidine
36. 4-[3-(α-naphthylureido)]-4-methoxycarbonyl-2,2,6,6-tetramethylpiperidine
37. 4-(3-cyclohexylureido)-4-methoxycarbonyl-2,2,6,6-tetramethylpiperidine
38. 4-(3,3-di-n-butylureido)-4-methoxycarbonyl-2,2,6,6-tetramethylpiperidine
39. 4-(1-piperidinecarbonamido)-4-methoxycarbonyl-2,2,6,6-tetramethylpiperidine
40. 4-(3-methylthioureido)-4-ethoxycarbonyl-2,2,6,6-tetramethylpiperidine
41. 4-acetamido-4-methoxycarbonyl-2,2,6,6-tetramethylpiperidine-1-oxyl
42. 4-benzamido-4-methoxycarbonyl-2,2,6,6-tetramethylpiperidine-1-oxyl
43. 4-amino-4-methoxycarbonyl-1,2,2,6,6-pentamethylpiperidine 44. 4-methylamino-4-methoxycarbonyl-1,2,2,6,6-pentamethylpiperidine
45. 4-allylamino-4-allyloxycarbonyl-1,2,2,6,6-pentamethylpiperidine
46. 4-acetamido-4-methoxycarbonyl-1,2,2,6,6-pentamethylpiperidine
47. 4-caprylamido-4-methoxycarbonyl-1,2,2,6,6-pentamethylpiperidine
48. 4-caprylamido-4-benzyloxycarbonyl-1,2,2,6,6-pentamethylpiperidine
49. 4-caprylamido-4-allyloxycarbonyl-1,2,2,6,6-pentamethylpiperidine
50. 4-caprylamido-4-ethoxymethoxycarbonyl-1,2,2,6,6-pentamethylpiperidine
51. 4-stearamido-4-methoxycarbonyl-1,2,2,6,6-pentamethylpiperidine
52. 4-acrylamido-4-methoxycarbonyl-1,2,2,6,6-pentamethylpiperidine
53. 4-benzamido-4-methoxycarbonyl-1,2,2,6,6-pentamethylpiperidine
54. 4-(o-methoxybenzamido)-4-methoxycarbonyl-1,2,2,6,6-pentamethylpiperidine
55. 4-(β-naphthamido)-4-ethoxycarbonyl-1,2,2,6,6-pentamethylpiperidine
56. 4-(anthraquinone-2-carbonamido)-4-methoxycarbonyl-1,2,2,6,6-pentamethylpiperidine
57. 4-cyclohexanecarbonamido-4-methoxycarbonyl-1,2,2,6,6-pentamethylpiperidine
58. 4-phenoxyacetamido-4-methoxycarbonyl-1,2,2,6,6-pentamethylpiperidine
59. 4-phenylacetamido-4-octadecyloxycarbonyl-1,2,2,6,6-pentamethylpiperidine
60. 4-[β-(3,5-di-t-butyl-4-hydroxyphenyl)propionamido]-4-methoxycarbonyl-1,2,2,6,6-pentamethylpiperidine
61. 4-benzenesulfonamido-4-n-butoxycarbonyl-1,2,2,6,6-pentamethylpiperidine
62. 4-ethoxycarbonamido-4-ethoxycarbonyl-1,2,2,6,6-pentamethylpiperidine
63. 4-benzyloxycarbonamido-4-methoxycarbonyl-1,2,2,6,6-pentamethylpiperidine
64. 4-(3-methylureido)-4-methoxycarbonyl-1,2,2,6,6-pentamethylpiperidine
65. 4-(3-n-butylureido)-4-methoxycarbonyl-1,2,2,6,6-pentamethylpiperidine
66. 4-(3-phenylureido)-4-methoxycarbonyl-1,2,2,6,6-pentamethylpiperidine
67. 4-(3-p-tolylureido)-4-(p-methylbenzyloxycarbonyl)-1,2,2,6,6-pentamethylpiperidine
68. 4-amino-4-n-butoxycarbonyl-1-n-butyl-2,2,6,6-tetramethylpiperidine
69. 4-(3-methylureido)-4-n-butoxycarbonyl-1-n-butyl-2,2,6,6-tetramethylpiperidine
70. 4-acetamido-4-methoxycarbonyl-1-allyl-2,2,6,6-tetramethylpiperidine
71. 4-acetamido-4-ethoxycarboxyl-1-(2-propynyl)-2,2,6,6-tetramethylpiperidine
72. 4-amino-4-methoxycarbonyl-1-benzyl-2,2,6,6-tetramethylpiperidine
73. 4-acetamido-4-ethoxycarbonyl-1-benzyl-2,2,6,6-tetramethylpiperidine
74. 4-benzamido-4-methoxycarbonyl-1-benzyl-2,2,6,6-tetramethylpiperidine
75. 4-(p-t-butylbenzamido)-4-methoxycarbonyl-1-benzyl-2,2,6,6-tetramethylpiperidine
76. 4-(o-hydroxybenzamido)-4-methoxycarbonyl-1-benzyl-2,2,6,6-tetramethylpiperidine
77. 4-(3-octadecylureido)-4-methoxycarbonyl-1-(p-methylbenzyl)-2,2,6,6-tetramethylpiperidine
78. 4-(3-phenylureido)-4-methoxycarbonyl-1-(p-chlorobenzyl)-2,2,6,6-tetramethylpiperidine
79. 4-crotonamido-4-methoxycarbonyl-1-cyanomethyl-2,2,6,6-tetramethylpiperidine
80. 4-acetamido-4-ethoxycarbonyl-1-cyanomethyl-2,2,6,6-tetramethylpiperidine
81. 4-acetamido-4-ethoxycarbonyl-1-(2,3-epoxypropyl)-2,2,6,6-tetramethylpiperidine
82. 4-(p-toluamido)-4-methoxycarbonyl-1-(2-ethoxyethyl)-2,2,6,6-tetramethylpiperidine
83. 4-propionamido-4-ethoxycarbonyl-1-(2-hydroxyethyl)-2,2,6,6-tetramethylpiperidine
84. 4-(2-acetoxyethylamino)-4-ethoxycarbonyl-1-(2-acetoxyethyl)-2,2,6,6-tetramethylpiperidine
85. 4-acetamido-4-methoxycarbonyl-1-(2-stearoyloxyethyl)-2,2,6,6-tetramethylpiperidine
86. 4-benzamido-4-methoxycarbonyl-1-(2-benzoyloxyethyl)-2,2,6,6-tetramethylpiperidine
87. 4-methacrylamido-4-methoxycarbonyl-1-(2-p-toluoyloxyethyl)-2,2,6,6,-tetramethylpiperidine
88. 4-(3-p-tolylureido)-4-methoxycarbonyl-1-(2-valeryloxypropyl)-2,2,6,6-tetramethylpiperidine
89. 4-benzamido-4-methoxycarbonyl-1-(2-phenyl-2-acetoxyethyl)-2,2,6,6-tetramethylpiperidine
90. 4-benzamido-4-methoxycarbonyl-1-(2-butyryloxyethyl)-2,2,6,6-tetramethylpiperidine
91. 4-benzamido-4-methoxycarbonyl-1-[2-(2-ethylhexanoyloxy)ethyl]-2,2,6,6-tetramethylpiperidine
92. 4-benzamido-4-methoxycarbonyl-1-(2-lauroyloxyethyl)-2,2,6,6-tetramethylpiperidine
93. 4-propionamido-4-ethoxycarbonyl-1-ethoxycarbonylmethyl-2,2,6,6-tetramethylpiperidine
94. 4-acetamido-4-ethoxycarbonyl-1-acetyl-2,2,6,6-etramethylpiperidine
95. 4-benzamido-4-methoxycarbonyl-1-acetyl-2,2,6,6-tetramethylpiperidine
96. 4-benzamido-4-methoxycarbonyl-1-acryloyl-2,2,6,6-tetramethylpiperidine
97. 4-benzamido-4-methoxycarbonyl-1-crotonoyl-2,2,6,6-tetramethylpiperidine
98. 4-acetamido-1-4-diethoxycarbonyl-2,2,6,6-tetramethylpiperidine
99. 1,3-bis-(4-methoxycarbonyl-2,2,6,6-tetramethyl-4-piperidyl)-urea
100. N,N'-bis-(4-ethoxycarbonyl-2,2,6,6-tetramethyl-4-piperidyl)-succinamide
101. N,N'-bis-(4-ethoxycarbonyl-2,2,6,6-tetramethyl-4-piperidyl)-3,3'-sebacamide
102. N,N'-bis-(4-methoxycarbonyl-2,2,6,6-tetramethyl-4-piperidyl)-3,3'-thiodipropionamide
103. N,N'-bis-(4-methoxycarbonyl-2,2,6,6-tetramethyl-4-piperidyl)-fumaramide
104. N,N'-bis-(4-methoxycarbonyl-2,2,6,6-tetramethyl-4-piperidyl)-terephthalamide
105. N,N'-bis-(4-octadecyloxycarbonyl-2,2,6,6-tetramethyl-4-piperidyl)isophthalamide
106. N,N'-bis-(4-methoxycarbonyl-2,2,6,6-tetramethyl-4-piperidyl)-cyclohexane-1,4-dicarbonamide
107. 1,1'-hexamethylenebis-[3-(4-methoxycarbonyl-2,2,6,6-tetramethyl-4-piperidyl)urea]
108. 1,1'-p-phenylenebis-[3-(4-methoxycarbonyl-2,2,6,6-tetramethyl-4-piperidyl)urea]
109. 1,1'-(4-methyl-1,3-phenylene)bis-[3-(4-methoxycarbonyl-2,2,6,6-tetramethyl-4-piperidyl)urea]
110. 1,1'-(1,5-naphthalene)bis-[3-(4-methoxycarbonyl-2,2,6,6-tetramethyl-4-piperidyl)urea]

111. 1,1'-p-xylylenebis-[3-(4-methoxycarbonyl-2,2,6,6-tetramethyl-4-piperidyl)urea]
112. 1,1'-(oxydi-p-phenylene)bis-[3-(4-methoxycarbonyl-2,2,6,6-tetramethyl-4-piperidyl)urea]
113. 1,1'-(methylenedi-p-phenylene)bis-[3-(4-methoxycarbonyl-2,2,6,6-tetramethyl-4-piperidyl)urea]
114. 1,1'-(4,4'-biphenylene)bis-[3-(4-methoxycarbonyl-2,2,6,6-tetramethyl-4-piperidyl)urea]
115. 4,4'-tetramethylenediiminobis-(4-methoxycarbonyl-1,2,2,6,6-pentamethylpiperidine)
116. 4,4'-(2-butenylene)diiminobis-(4-methoxycarbonyl-1,2,2,6,6-pentamethylpiperidine).
117. 4,4'-p-xylylenediiminobis-(4-methoxycarbonyl-1,2,2,6,6-pentamethylpiperidine)
118. N,N'-bis-(4-methoxycarbonyl-1,2,2,6,6-pentamethyl-4-piperidyl) sebacamide
119. N,N'-bis-(4-methoxycarbonyl-1,2,2,6,6-pentamethyl-4-piperidyl) terephthalamide
120. N,N'-bis-(4-allyloxycarbonyl-1,2,2,6,6-pentamethyl-4-piperidyl) isophthalamide
121. N,N'-bis-(4-n-butoxycarbonyl-1-n-butyl-2,2,6,6-tetramethyl-4-piperidyl) naphthalene-1,5-dicarbonamide
122. N,N'-bis-(4-methoxycarbonyl-1-allyl-2,2,6,6-tetramethyl-4-piperidyl) 1,10-decanedicarbonamide
123. N,N'-bis-(4-methoxycarbonyl-1-benzyl-2,2,6,6-tetramethyl-4-piperidyl) sebacamide
124. N,N'-bis-[4-octyloxycarbonly-1-(2,3-epoxypropyl)-2,2,6,6-tetramethyl-4-piperidyl]isophthalamide
125. 1,1'-tetramethylenebis 3-[4-ethoxycarbonyl-1-(2-acetoxyethyl)-2,2,6,6-tetramethyl-4-piperidyl]urea
126. N,N'-bis-[4-ethoxycarbonyl-1-(2-stearoyloxyethyl)-2,2,6,6-tetramethyl-4-piperidyl] terephthalamide
127. N,N'-bis-[4-ethoxycarbonyl-1-(2-benzoyloxyethyl)-2,2,6,6-tetramethyl-4-piperidyl] isophthalamide
128. N,N',N'''-tris-(4-methoxycarbonyl-2,2,6,6-tetramethyl-4-piperidyl) trimesamide
129. N,N',N'''-tris-(4-ethoxycarbonyl-2,2,6,6-tetramethyl-4-piperidyl) trimelitamide
130. 4-benzamido-4-ethoxycarbonyl-2,6-diethyl-2,3,6-trimethylpiperidine
131. 4-(3-methylureido)-4-ethoxycarbonyl-2,6-diethyl-2,3,6-trimethylpiperidine
132. 4-acetamido-4-octadecyloxycarbonyl-1-octadecyl-2,2,6,6-tetramethylpiperidine
133. 4-acetamido-4-ethoxycarbonyl-1-(2-hexadecyloxyethyl)-2,2,6,6-tetramethylpiperidine
134. 4-acetamido-4-ethoxycarbonyl-1-crotonoyl-2,2,6,6-tetramethylpiperidine
135. 4-benzamido-4-ethoxycarbonyl-1-(p-methoxybenzyl)-2,2,6,6-tetramethylpiperidine
136. 4-benzamido-4-ethoxycarbonyl-1-(2-crotonoyloxyethyl)-2,2,6,6-tetramethylpiperidine
137. 4-benzamido-4-ethoxycarbonyl-1-(2-o-chlorobenzoyloxyethyl)-2,2,6,6-tetramethylpiperidine
138. 4-benzamido-4-ethoxycarbonyl-1-(2-p-methoxybenzoyloxyethyl)-2,2,6,6-tetramethylpiperidine
139. 4-benzamido-4-ethoxycarbonyl-1-(2-salicyloyloxethyl)-2,2,6,6-tetramethylpiperidine
140. 4-benzamido-4-ethoxycarbonyl-1-(2-phenylacetoxyethyl)-2,2,6,6-tetramethylpiperidine
141. 4-benzamido-4-ethoxycarbonyl-1-(2-p-chlorophenylacetoxyethyl)-2,2,6,6-tetramethylpiperidine
142. 4-benzamido-4-ethoxycarbonyl-1-(2-p-methoxyphenylacetoxyethyl)-2,2,6,6-tetramethylpiperidine
143. 4-benzamido-4-ethoxycarbonyl-1-(2-p-tolylacetoxyethyl)-2,2,6,6-tetramethylpiperidine
144. 4-benzamido-4-ethoxycarbonyl-1-{2-[β-(3,5-di-t-butyl-4-hydroxyphenyl)propionyloxy]ethyl}-2,2,6,6-tetramethylpiperidine
145. 4-benzamido-4-ethoxycarbonyl-1-(2-cinnamoyloxyethyl)-2,2,6,6-tetramethylpiperidine
146. 4-benzamido-4-ethoxycarbonyl-1-(2-cyclohexanecarbonyloxyethyl)-2,2,6,6-tetramethylpiperidine
147. 4-acetamido-4-methoxycarbonyl-1-(2-butenyloxycarbonylmethyl)-2,2,6,6-tetramethylpiperidine
148. 4-acetamido-4-methoxycarbonyl-1-octadecyloxycarbonylmethyl-2,2,6,6-tetramethylpiperidine
149. 4-acetamido-4-methoxycarbonyl-1-phenoxycarbonylmethyl-2,2,6,6-tetramethylpiperidine
150. 4-acetamido-4-methoxycarbonyl-1-benzyloxycarbonylmethyl-2,2,6,6-tetramethylpiperidine
151. 4-acetamido-4-methoxycarbonyl-1-cyclohexyloxycarbonylmethyl-2,2,6,6-tetramethylpiperidine
152. 4-acetamido-4-methoxycarbonyl-1-octoxycarbonyl-2,2,6,6-tetramethylpiperidine
153. 4-acetamido-4-methoxycarbonyl-1-benzyloxycarbonyl-2,2,6,6-tetramethylpiperidine
154. 4-acetamido-4-methoxycarbonyl-1-phenoxycarbonyl-2,2,6,6-tetramethylpiperidine
155. 4-acetamido-4-(p-octoxybenzyloxycarbonyl)-2,2,6,6-tetramethylpiperidine
156. 4-octadecylamino-4-ethoxycarbonyl-2,2,6,6-tetramethylpiperidine
157. 4-(m-chlorobenzamido)-4-ethoxycarbonyl-2,2,6,6-tetramethylpiperidine
158. 4-(p-octoxybenzamido)-4-ethoxycarbonyl-2,2,6,6-tetramethylpiperidine
159. 4-(m-chlorobenzylamino)-4-ethoxycarbonyl-2,2,6,6-tetramethylpiperidine
160. 4-(p-methylbenzylamino)-4-ethoxycarbonyl-2,2,6,6-tetramethylpiperidine
161. 4-(p-n-butoxybenzylamino)-4-ethoxycarbonyl-2,2,6,6-tetramethylpiperidine
162. 4-(2-crotonoyloxyethyl)-4-ethoxycarbonyl-1,2,2,6,6-pentamethylpiperidine
163. 4-(2-stearoyloxyethyl)-4-ethoxycarbonyl-1,2,2,6,6-pentamethylpiperidine
164. 4-(2-o-chlorobenzoyloxyethyl)-4-ethoxycarbonyl-1,2,2,6,6-pentamethylpiperidine
165. 4-(2-m-toluoyloxyethyl)-4-ethoxycarbonyl-1,2,2,6,6-pentamethylpiperidine
166. 4-(2-p-methoxybenzoyloxyethyl)-4-ethoxycarbonyl-1,2,2,6,6-pentamethylpiperidine
167. 4-(2-salicyloyloxyethyl)-4-ethoxycarbonyl-1,2,2,6,6-pentamethylpiperidine
168. 4-(2-phenylacetoxyethyl)-4-ethoxycarbonyl-1,2,2,6,6-pentamethylpiperidine
169. 4-(2-p-chlorophenylacetoxyethyl)-4-ethoxycarbonyl-1,2,2,6,6-pentamethylpiperidine
170. 4-(2-p-methylphenylacetoxyethyl)-4-ethoxycarbonyl-1,2,2,6,6-pentamethylpiperidine
171. 4-(2-p-methoxyphenylacetoxyethyl)-4-ethoxycarbonyl-1,2,2,6,6-pentamethylpiperidine
172. 4-{2-[β-(3,5-di-t-butyl-4-hydroxyphenyl)propionyloxy]ethyl}-4-ethoxycarbonyl-1,2,2,6,6-pentamethylpiperidine
173. 4-(2-cinnamoyloxyethyl)-4-ethoxycarbonyl-1,2,2,6,6-pentamethylpiperidine
174. 4-(2-cyclohexanecarbonyloxyethyl)-4-ethoxycarbonyl-1,2,2,6,6-pentamethylpiperidine
175. 4-octoxycarbonylamino-4-methoxycarbonyl-2,2,6,6-tetramethylpiperidine
176. 4-(3-benzylureido)-4-methoxycarbonyl-2,2,6,6-tetramethylpiperidine 177. 4-(3-phenylthioureido)-4-methoxycarbonyl-2,2,6,6-tetramethylpiperidine
178. bis-(4-methoxycarbonyl-2,2,6,6-tetramethyl-4-piperidylamino)-sulfoxide
179. bis-(4-methoxycarbonyl-2,2,6,6-tetramethyl-4-piperidylamino)-sulfone
180. N,N'-bis-(4-methoxycarbonyl-2,2,6,6-tetramethyl-4-piperidyl)-oxalylamide
181. 1,1'-(3,3'-dimethyl-4,4'-biphenylene)bis-[3-(4-methoxycarbonyl-4-piperidyl)urea]
182. 1,3,5-tris-(4-methoxycarbonyl-2,2,6,6-tetramethyl-4-piperidylaminomethyl)benzene
183. tris-(4-methoxycarbonyl-2,2,6,6-tetramethyl-4-piperidyl)phosphoramide Examples of the acid-addition salts provided by the invention include the oxalate and p-t-butylbenzoate of compound No. 2 in the above list, and the p-toluenesulfonate of compound No. 43 in the above list. Such acid-addition salts can be prepared from the corresponding pyridine derivatives of formula (I) by the conventional known techniques of salification.

The piperidine derivatives of formula (I) can be prepared as summarized in the following reaction scheme (wherein R, X, Y, Z and n have the meanings previously defined):

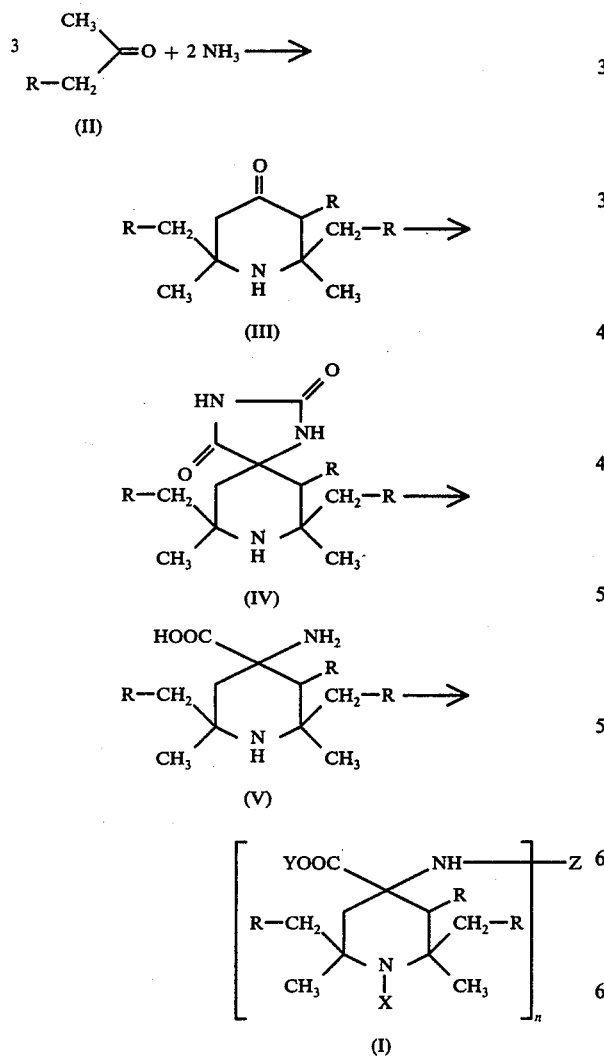

The reaction steps shown in the scheme can be carried out by the following methods:

1. Compounds of formula (III) are prepared by treating ketones of formula (II) with ammonia in an alcohol, over a prolonged period of time, by the method described in Berichte 41, 777 (1908).

2. Compounds of formula (IV) are prepared by reacting compounds of formula (III) with an alkali metal cyanide and ammonium carbonate.

3. Compounds of formula (V) are prepared by hydrolyzing compounds of formula (IV), by the method described in Bull. Soc. Chim. Fr. 1967, 815.

4. Compounds of formula (I) are prepared by introducing the substituent Y and, for meanings of X and Z other than hydrogen, also the substituents X and Z into the compounds of formula (V). The order in which these substituents are introduced is chosen, in accordance with the nature of the substituents, so that the reactions involved have no adverse effect on other parts of the molecule.

(A) The substituent X on the nitrogen atom of the piperidine nucleus can be introduced by means of the following methods:

(a) Compounds wherein X is alkyl, alkenyl, 2-propynyl, alkoxyalkyl, cyanoalkyl, aliphatic acyl, 2,3-epoxypropyl, aralkyl optionally substituted in its aryl moiety, $-CH_2CH(R^1)OR^2$, $-CH_2COOR^3$ or $-COOR^4$, all as defined for formula (I), can be prepared by using a halide of the desired substituent.

(b) Compounds wherein X is oxyl can be prepared by using a peroxide such as m-chloroperbenzoic acid or hydrogen peroxide.

(c) Compounds wherein the substituent X is $-CH_2CH(R^1)OH$, as previously defined, can also be prepared by using ethylene oxide, propylene oxide or styrene oxide; and the products can optionally be acylated to obtain the corresponding acylated derivatives wherein X is $-CH_2CH(R^1)OR^2$.

(d) Compounds wherein X is methyl are preferably prepared by the Leuckart-Wallach reaction, using formic acid and formaldehyde.

(e) Compounds wherein X is cyanomethyl are preferably prepared by reaction with formaldehyde and acetone cyanhydrin.

(B) Introduction of the substituent Y on the carboxyl group can be carried out by means of the conventional esterification reactions which are known per se.

(C) Introduction of the substituent Z on the amino group can be carried out by the following methods:

(a) Compounds wherein Z is alkyl, alkenyl, aliphatic acyl, aromatic, acyl, cinnamoyl, 3-(3,5-di-t-butyl-4-hydroxephenyl)propionyl, phenylacetyl, phenoxyacetyl, cyclohexanecarbonyl, aralkyl optionally substituted in its aryl moiety, $-CH_2CH_2OR^5$, $-SO_2R^6$, $-COOR^7$, alkylene, 2-butenylene, p-xylylene, carbonyl, sulfinyl, sulfonyl, oxalyl, $-CO-R^{11}-CO-$,

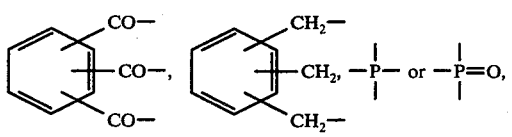

all as defined for formula (I), can be prepared by using the halide of the desired substituent.

(b) Compounds wherein Z is —CONR$^8$R$^9$ or —CONH—R$^{12}$—NHCO—, as previously defined, can be prepared by reaction with the corresponding isocyanates.

(c) Compounds wherein Z is —CSNHR$^{10}$, as previously defined, can be prepared by reaction with the corresponding isothiocyanates.

5. When the substituent X is a group unaffected by hydrolysis, such as alkyl or aralkyl, the compounds of formula (I) can alternatively be prepared by first introducing the substituent X on the nitrogen atom of the piperidine nucleus of compounds of formula (III), forming the corresponding spiro-hydantoin derivative by the method described in paragraph 2 above, hydrolyzing the spyro-hydantoin by the method described in paragraph 3 above, and then introducing the substituents Y and Z by the above-mentioned methods. As a yet further alternative, the substituent X can be introduced on the nitrogen atom of the spyro-hydantoin derivative (IV), which is then subjected to hydrolysis in the above-described manner, and finally the substituents Y and Z are introduced.

Piperidine derivatives of formula (I) prepared by any of these methods can optionally be salified by the conventional techniques known per se, in order to obtain the aforementioned acid-addition salts.

The following are individual examples of the 4-piperidone derivatives of formula (III):

| | |
|---|---|
| 2,2,6,6-tetramethyl-4-piperidone | bp 95–99° C/10 mmHg |
| 2,6-diethyl-2,3,6-trimethyl-4-piperidone | bp 91–93° C/2.0 mmHg |
| 3-ethyl-2,6-dimethyl-2,6-di-n-propyl-4-piperidone | bp 115–118° C/1.5 mmHg |
| 2,6-diisobutyl-2,6-dimethyl-3-isopropyl-4-piperidone | bp 129–131° C/2.0 mmHg |

The following are individual examples of the spyro-hydantoin derivatives of formula (IV):

| |
|---|
| 7,7,9,9-tetramethyl-1,3,8-triazaspiro[4.5]decane-2,4-dione<br>mp 260° C |
| 7,9-diethyl-6,7,9-trimethyl-1,3,8-triazaspiro[4.5]decane-2,4-dione<br>mp 263–267° C(decomposition) |
| 6-ethyl-7,9-dimethyl-7,9-di-n-propyl-1,3,8-triazaspiro[4.5]decane-2,4-dione<br>TLC:R$_f$=0.42 (silica gel, ethyl acetate:n-hexane :triethyl amine=10:5:2) |

The piperidine derivatives of formula (I) and their acid-addition salts are useful for stabilizing polymers, particularly synthetic polymers, against the deterioration caused by heat and/or light. Accordingly, the invention further provides a polymeric composition comprising a polymer and, as stabilizer, a piperidine derivative of formula (I) or an acid-addition salt thereof. Organic polymers which can be stabilized in this way include:

olefin and diene polymers including homopolymers of olefins and dienes (e.g. low-density, high-density and cross-linked polyethylenes, polypropylene, polyisobutylene, polymethylbutene-1, polymethylpentene-1, polyisoprene, and polybutadiene), mixtures of such homopolymers (e.g. mixtures of polypropylene and polyethylene, polypropylene and polybutene-1, or polypropylene and polyisobutylene), and copolymers of olefins and dienes (e.g. ethylene/propylene copolymers, propylene/butene-1 copolymers, propylene/isobutylene copolymers, ethylene/butene-1 copolymers, and terpolymers of ethylene and propylene with dienes such as hexadiene, dicyclopentadiene or ethylidene norbornene);

styrene polymers including polystyrene, copolymers of styrene and of α-methylstyrene (e.g. styrene/butadiene copolymers, styrene/acrylonitrile copolymers, styrene/acrylonitrile/methylmethacrylate copolymers, styrene/acrylonitrile/acrylic ester copolymers, styrene/acrylonitrile copolymers modified with acrylic ester polymers to provide impact strength, and styrene polymers modified with ethylene/propylene/diene elastomers to provide impact strength), and graft copolymers of styrene (e.g. polymers in which styrene is grafted onto polybutadiene, and polymers in which styrene and acrylonitrile are grafted onto polybutadiene as well as mixtures thereof with the aforementioned styrene copolymers — commonly known as acrylonitrile/butadiene/styrene or ABS plastics);

halogenated vinyl and vinylidene polymers including polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, and vinylidene chloride/vinyl acetate copolymers;

polymers derived from α,β-unsaturated acids and derivatives thereof, including polyacrylates and polymethacrylates, polyacrylic amides and polyacrylonitrile;

polymers derived from unsaturated alcohols and amines and from the acyl derivatives thereof or acetals, including polyvinyl alcohol, polyvinyl acetate, polyvinyl stearate, polyvinyl benzoate, polyvinyl maleate, polyvinyl butyral, polyallyl phthalate, and polyallyl melamine, and copolymers thereof with other ethylenically unsaturated monomers (e.g. ethylene/vinyl acetate copolymers);

epoxy polymers including homopolymers and copolymers derived from epoxides (e.g. polyethylene oxide), and polymers derived from bis-glycidyl ethers;

polyacetals, polyalkylene oxides and polyphenylene oxides including polyoxymethylene, oxymethylene/ethylene oxide copolymers, polyoxyethylene, polypropylene oxide, polyisobutylene oxide and polyphenylene oxides;

polyurethanes and polyureas;

polycarbonates;

polysulphones;

polyamides and copolyamides derived from diamines and dicarboxylic acids and/or from aminocarboxylic acids or the corresponding lactams, including nylon-6, nylon-6,6, nylon-6,10, nylon-11 and nylon-12;

polyesters derived from dicarboxylic acids and dialcohols and/or from hydroxycarboxylic acids and the corresponding lactones, e.g. polyethylene glycol terephthalate and poly-1,4-dimethylol-cyclohexane terephthalate;

cross-linked polymers derived from aldehydes together with phenols, ureas or melamines, e.g. phenol/formaldehyde, urea/formaldehyde and melamine/formaldehyde resins;

alkyd resins e.g. glycerol/phthalic acid resins and mixtures thereof with melamine/formaldehyde resins;

unsaturated polyester resins derived from copolyesters of saturated and unsaturated dicarboxylic acids with polyhydric alcohols as well as from vinyl compounds as cross-linking agents, and also halogenated flame-resistant modifications thereof; and natural polymers including cellulose, rubber and proteins, as well as chemically modified homologues thereof (e.g. cellulose acetates, cellulose propionates, cellulose butyrates and cellulose ethers such as methyl cellulose).

The amount of the stabilizers of the invention needed for effective stabilization of organic polymers will depend on a variety of factors, such as the type and properties of the polymer concerned, its intended use, and the presence of other stabilizers. It is generally satisfactory to use from 0.01% to 5% by weight of the stabilizers of the invention, based on the weight of the polymer, but the most effective range will vary with the type of polymer: viz. 0.01% to 2.0%, preferably 0.02% to 1.0%, by weight for olefin, diene and styrene polymers; 0.01% to 1.0%, preferably 0.02% to 0.5%, by weight for vinyl and vinylidene polymers; and 0.01% to 5.0%, preferably 0.02% to 2.0%, by weight for polyurethanes and polyamides. If desired, two or more of the stabilizers of the invention may be used together.

The stabilizers of the invention may readily be incorporated into organic polymers by conventional techniques at any convenient stage prior to the manufacture of shaped articles therefrom. For example, the stabilizer may be mixed with the polymer in dry powder form, or a suspension of emulsion of the stabilizer may be mixed with a solution, suspension or emulsion of the polymer.

The stabilized polymeric compositions of the invention may optionally also contain one or more of various additives conventionally used in polymer technology, such as the additives listed in British patent specification No. 1 401 924, at pages 11-13.

The invention is further illustrated by the following non-limiting Examples, in which all parts and percentages are by weight. Examples 1-8 illustrate the preparation of the piperidine derivatives of formula (I). Examples 9-14 illustrate the use of said piperidine derivatives as stabilizers for synthetic polymers, and the test compounds used in them are identified by means of the numbers appended to the compounds in the list given hereinbefore.

EXAMPLE 1

4-amino-4-ethoxycarbonyl-2,2,6,6-tetramethylpiperidine 150 ml of ethanol were added to 55 g of 4-amino-4-carboxy-2,2,6,6-tetramethylpiperidine, and then 30 ml of concentrated sulfuric acid were added dropwise to the mixture under stirring at 20°-30° C. The resulting mixture was refluxed for 1 hour.

After completion of the reaction water was added to the reaction mixture which was then saturated with sodium carbonate and extracted with ether. The ether extract was dried over sodium sulfate and the solvent was removed. Distillation of the residue under reduced pressure gave 13 g of the desired product as a liquid boiling at 105°-107° C./5 mmHg.

EXAMPLE 2

4-acetamido-4-ethoxycarbonyl-2,2,6,6-tetramethylpiperidine 13 g of 4-amino-4-ethoxycarbonyl-2,2,6,6-tetramethylpiperidine, obtained by the procedure of Example 1, were dissolved in 50 ml of ether, and a solution of 9 g of acetyl chloride in 30 ml of ether was added dropwise at 5°-10° C. with stirring. The resulting mixture was refluxed for 2 hours. After completion of the reaction, saturated potassium carbonate solution was added to the reaction mixture which was then extracted with ethyl acetate. The solvent was removed from the extract and the residue was recrystallized from ethyl acetate, giving 8 g of the desired product as crystals melting at 108°-109° C.

EXAMPLE 3

4-acetamido-4-ethoxycarbonyl-1-(2,3-epoxypropyl)-2,2,6,6-tetramethylpiperidine 3 g of α-epibromohydrin and 0.5 g of potassium carbonate were added to 1 g of 4-acetamido-4-ethoxycarbonyl-2,2,6,6-tetramethylpiperidine obtained by the procedure of Example 2, and the resulting mixture was heated with stirring for 3 hours at 100° C.

After completion of the reaction, 10% potassium carbonate solution was added to the reaction mixture which was then extracted with ethyl acetate. The extract was washed with water and dried over sodium sulfate. After removal of the solvent, the residue was recrystallized from ethyl acetate giving 0.85 g of the desired product as crystals melting at 139°-141° C.

EXAMPLE 4

4-acetamido-4-ethoxycarbonyl-1-cyanomethyl-2,2,6,6-tetramethylpiperidine 0.9 g of 37% formalin solution and 2 ml of acetone cyanohydrin were added to 1 g of 4-acetamido-4-ethoxycarbonyl-2,2,6,6-tetramethylpiperidine obtained by the procedure of Example 2. The resulting mixture was stirred at room temperature, 0.4 ml of 0.1 N-sodium hydroxide solution was added to it, and the mixture was then stirred at room temperature for 3 hours.

The crystals which precipitated were filtered off, washed with potassium carbonate solution and then recrystallized from ethyl acetate, giving 0.8 g of the desired product as crystals melting at 120°-121° C.

EXAMPLE 5

4-caprylamido-4-benzoyloxycarbonyl-1,2,2,6,6-pentamethylpiperidine 239 g of 7,7,8,9,9-pentamethyl-1,3,8-triazaspiro[4.5]-decane-2,4-dione and 790 g of barium hydroxide octahydrate were added to 2.5 liters of water and the resulting mixture was refluxed for 72 hours under stirring. The mixture was then filtered hot and the residue was washed with hot water. The filtrate and washings were combined, 500 g of ammonium carbonate were added, and the mixture was refluxed until evolution of gaseous ammonia ceased.

After completion of the reaction, the reaction mixture was cooled and filtered. The filtrate was concentrated and ethanol was added to the residue. The crystals which precipitated were filtered off, giving 122 g of 4-amino-4-carboxy-1,2,2,6,6-pentamethylpiperidine melting at 250°-251° C. (with decomposition).

27.5 g of the 4-amino-4-carboxy-1,2,2,6,6-pentamethylpiperidine thus obtained were added to 150 ml of benzene, and a solution of 23 g of capryloyl chloride in 50 ml of benzene was added to the mixture under water-cooling and with stirring. The resulting mixture was refluxed for 3 hours and the benzene was then removed under reduced pressure, giving 43 g of crystals of crude 4-caprylamido-4-carboxy-1,2,2,6,6-pentamethylpiperidine hydrochloride.

5 g of the 4-caprylamido-4-carboxy-1,2,2,6,6-pentamethylpiperidine hydrochloride thus obtained were added to 30 ml of xylene, then 2.2 g of potassium carbonate were added to the mixture, and the whole was refluxed for 1 hour under stirring. 2.3 g of benzyl bromide were added to the reaction mixture, which was then refluxed for a further hour.

After completion of the reaction, the reaction mixture was cooled, 10% sodium carbonate solution was added, and the mixture was extracted with ethyl acetate. The extract was washed with water and dried over sodium sulfate, and the solvent was removed. Distillation of the residue under reduced pressure gave 1.5 g of the desired product as an oil boiling at 200°–202° C./0.1 mmHg.

EXAMPLE 6

4-amino-4-methoxycarbonyl-1,2,2,6,6-pentamethylpiperidine 5 g of 4-amino-4-carboxy-1,2,2,6,6-pentamethylpiperidine, obtained by the procedure of Example 5, and 20 ml of concentrated sulfuric acid were added to 150 ml of methanol. The mixture was refluxed for 20 hours in a flask fitted with a Soxhlet extractor charged with 120 g of molecular sieve 4A which had been dried for 3 hours under direct heating.

After completion of the reaction, the reaction mixture was concentrated. Saturated potassium carbonate solution was added to the residue and it was extracted with benzene. The extract was dried over sodium sulfate and the solvent was removed. Distillation of the resulting residue under reduced pressure gave 16 g of the desired product as an oil boiling at 106°–107° C./0.5 mmHg.

EXAMPLE 7

4-(3-phenylureido)-4-methoxycarbonyl-1,2,2,6,6-pentamethylpiperidine 0.5 g of 4-amino-4-methoxycarbonyl-1,2,2,6,6-pentamethylpiperidine, obtained by the procedure of Example 6, was dissolved in 5 ml of ether. To this solution was added a solution of 0.5 g of phenyl isocyanate in 5 ml of ether, and the resulting mixture was refluxed for 3 hours.

After completion of the reaction, the reaction mixture was concentrated, and the resulting residue was recrystallized from ethyl acetate, giving 0.7 g of the desired product as crystals melting at 159°–160° C. (with decomposition).

EXAMPLE 8

4-benzyloxycarbonamido-4-methoxycarbonyl-1,2,2,6,6-pentamethylpiperidine 0.9 g of 4-amino-4-methoxycarbonyl-1,2,2,6,6-pentamethylpiperidine, obtained by the procedure of Example 6, was dissolved in 15 ml of ether. To this solution was added dropwise a solution of 0.9 g of carbobenzoxy chloride in 10 ml of ether, under ice-cooling and with stirring, and the resulting mixture was refluxed for 1 hour.

After completion of the reaction, the reaction mixture was neutralized with potassium carbonate solution and extracted with ethyl acetate. The solvent was removed from the extract and the resulting residue was recrystallized from a mixture of ethyl acetate and ether, giving 1.1 g of the desired product as crystals melting at 117°–118° C.

Substantially the same procedures as described in the foregoing Examples were used to prepare the following compounds:

---

4-crotonamido-4-methoxycarbonyl-2,2,6,6-tetramethylpiperidine
   mp 121–122° C 4-benzamido-4-methoxycarbonyl-2,2,6,6-tetramethylpiperidine
   mp 166–167° C 4-allylamino-4-allyloxycarbonyl-1,2,2,6,6-pentamethylpiperidine
   bp 125–127° C/0.1 mmHg 4-caprylamido-4-methoxycarbonyl-1,2,2,6,6-pentamethylpiperidine
   mp 64–65° C 4-caprylamido-4-allyloxycarbonyl-1,2,2,6,6-pentamethylpiperidine
   bp 190-195° C/0.3 mmHg 4-caprylamido-4-ethoxymethoxycarbonyl-1,2,2,6,6-pentamethylpiperidine
   bp 155–157° C/0.3 mmHg 4-stearamido-4-methoxycarbonyl-1,2,2,6,6-pentamethylpiperidine
   mp 62–64° C 4-acrylamido-4-methoxycarbonyl-1,2,2,6,6-pentamethylpiperidine
   mp 180–181° C 4-(o-methoxybenzamido)-4-methoxycarbonyl-1,2,2,6,6-pentamethylpiperidine
   mp 151° C 4-(anthraquinone-2-carbonamido)-4-methoxycarbonyl-1,2,2,6,6-pentamethylpiperidine
   mp 227–229° C 4-cyclohexanecarbonamido-4-methoxycarbonyl-1,2,2,6,6-pentamethylpiperidine
   mp 166–168° C 4-phenoxyacetamido-4-methoxycarbonyl-1,2,2,6,6-pentamethylpiperidine
   mp 78–80° C 4-acetamido-4-methoxycarbonyl-1-allyl-2,2,6,6-tetramethylpiperidine
   mp 127–129° C 4-acetamido-4-ethoxycarbonyl-1-(2-propynyl)-2,2,6,6-tetramethylpiperidine
   mp 150–152° C 4-acetamido-4-ethoxycarbonyl-1-benzyl-2,2,6,6-tetramethylpiperidine
   mp 154–155° C 4-crotonamido-4-methoxycarbonyl-1-cyanomethyl-2,2,6,6-tetramethylpiperidine
   mp 194–195° C N,N'-bis(4-methoxycarbonyl-1,2,2,6,6-pentamethyl-4-piperidyl)-terephthalamide
   mp >210° C 4-benzamido-4-methoxycarbonyl-1,2,2,6,6-pentamethylpiperidine
   mp 151–152° C 4-benzamido-4-methoxycarbonyl-1-acetyl-2,2,6,6-tetramethylpiperidine
   mp 203–204° C

---

EXAMPLE 9

Mixtures were made from 100 parts of polypropylene [Noblen JHH-G, trade name of Mitsui Toatsu Chemicals Inc., employed after two recrystallizations from monochlorobenzene] and 0.25 part of each in turn of the stabilizers of the invention in Table 1 or, as a control, of the known stabilizer "Tinuvin 327". The resulting mixtures were blended, melted, and moulded under heating and pressure into sheets 0.5 mm thick. A control sheet, containing no stabilizer, was also made.

The sheets thus formed were exposed to ultraviolet irradiation at 45° C. in a "Fade-O-Meter" (trade mark). The time required for each sheet to become brittle is shown in Table 1.

Table 1

| Stabilizer No. | Polypropylene |
| --- | --- |
| 2 | 540 |
| 9 | 760 |
| 17 | 1000 |
| 18 | 1080 |
| 43 | 1080 |
| 45 | 600 |
| 47 | 960 |
| 48 | 920 |
| 49 | 1080 |
| 50 | 960 |
| 51 | 1040 |
| 52 | 1100 |
| 53 | 700 |
| 54 | 540 |
| 56 | 1100 |
| 57 | 1100 |
| 58 | 800 |
| 70 | 700 |
| 71 | 920 |
| 73 | 680 |
| 79 | 920 |
| 80 | 840 |
| 81 | 720 |
| None | 60 |
| Tinuvin 327 | 340 |

Tinuvin 327 : 2-(2-hydroxy-3,5-di-t-butylphenyl)-5-chlorobenzo-1,2,3-triazole.

EXAMPLE 10

Mixtures were made from 100 parts of high density polyethylene ("Hi-Zex", trade name of Mitsui Toatsu Chemicals Inc., employed after two recrystallizations from toluene) and 0.25 part of each in turn of the stabilizers of the invention indicated in Table 2 or, as a control, of the known stabilizer "Tinuvin 327". The resulting mixtures were moulded under heating and pressure into sheets 0.5 mm thick. A control sheet, containing no stabilizer, was also made.

The brittleness time of each sheet was measured by the same method as in Example 9, and the results are shown in Table 2.

Table 2

| Stabilizer No. | High density polyethylene |
| --- | --- |
| 9 | 1620 |
| 18 | 2140 |
| 47 | 2180 |
| 48 | 2060 |
| 51 | 2200 |
| 73 | 1600 |
| None | 360 |
| Tinuvin 327 | 700 |

Tinuvin 327: 2-(2-hydroxy-3,5-di-t-butylphenyl)-5-chlorobenzo-1,2,3-triazole.

EXAMPLE 11

Mixtures were made from 100 parts of acrylonitrile-/butadiene/styrene resin ["Kane Ace B-12", trade name of Kanegafuchi Chemical Industries Co. Ltd.] and 0.5 part of each in turn of the stabilizers of the invention indicated in Table 3. The resulting mixtures were kneaded for 6 minutes on kneading rolls at 160° C. and then moulded into sheets about 0.5 mm thick. A control sheet, containing no stabilizer, was also made.

The sheets thus formed were exposed for 50 hours in a "Sunshine Weather-O-Meter". The retention of ultimate elongation and of ultimate tensile strength of the sheets were measured by standard methods, and the results are shown in Table 3.

Table 3

| Stabilizer No. | Retention of elongation (%) | Retention of tensile strength (%) |
| --- | --- | --- |
| 9 | 63 | 74 |
| 18 | 68 | 78 |
| 48 | 64 | 80 |
| 49 | 68 | 79 |
| 51 | 70 | 78 |
| 52 | 71 | 83 |
| 70 | 69 | 81 |
| 73 | 65 | 76 |
| None | 51 | 65 |

EXAMPLE 12

Mixtures were made from 100 parts of nylon-6 resin ["CM1041", trade name of Toray Indsutries Inc.] and 0.25 part of each in turn of the stabilizers of the invention indicated in Table 4. The resulting mixtures were melted, and moulded under pressure into films about 0.1 mm thick in a conventional compression-moulding machine. A control film, contaning no stabilizer, was also made.

The films thus formed were aged under the conditions described below, and their retention of ultimate tensile strength and of ultimate elongation were measured by standard methods. The results are shown in Table 4.

Aging conditions:
1. exposure to ultraviolet irradiation for 200 hours at 45° C. in a "Fade-O-Meter".
2. aging for 2 hours at 160° C. in a Geer's aging tester.

Table 4

| Stabilizer No. | Fade-O-Meter | | Geer's aging tester | |
| --- | --- | --- | --- | --- |
| | retention of elongation (%) | retention of tensile strength (%) | retention of elongation (%) | retention of tensile strength (%) |
| 9 | 64 | 69 | 67 | 69 |
| 18 | 68 | 72 | 71 | 76 |
| 47 | 72 | 78 | 73 | 81 |
| 52 | 66 | 80 | 70 | 78 |
| 70 | 71 | 83 | 68 | 80 |
| 73 | 65 | 79 | 68 | 77 |
| None | 52 | 50 | 55 | 56 |

EXAMPLE 13

Mixtures were made from 100 parts of polyester-type polyurethane ["Paraprene pellet 22S", trade name of Nippon Polyurethane Industries, Co. Ltd.], 400 parts of tetrahydrofuran and 1 part of each in turn of the stabilizers of the invention indicated in Table 5. The resulting solutions were used to cast films about 0.1 mm thick on a plane glass plate, and the films were then dried. A control film, containing no stabilizer, was also made. The films thus formed were exposed to ultraviolet irradiation for 400 hours at 45° C. in a "Sunshine Weather-O-Meter". The difference in colour before and after the exposure to ultraviolet irradiation was measured on test-pieces of the films, by the method prescribed in Japanese Industrial Standard K-7103, using a colour-difference colorimeter; and the change in their "yellowness index" was calculated by means of the equation:

$$\Delta YI = YI - YI_o$$

wherein $\Delta YI$ is the change in the yellowness index, $YI$ is the yellowness index after exposure, and $YI_o$ is the initial yellowness index of the test piece. The results are shown in Table 5.

Table 5

| Stabilizer No. | ΔYI |
|---|---|
| 9 | 25.9 |
| 47 | 25.4 |
| 52 | 24.8 |
| 70 | 24.2 |
| 73 | 24.7 |
| None | 51.9 |

EXAMPLE 14

Mixtures were made from 100 parts of polyvinyl chloride ["Geon 103EP", trade name of the Nippon Geon Co. Ltd.], 3 parts of dibutyl tin maleate, 0.5 part of butyl stearate and 0.25 part of each in turn of the stabilizers of the invention indicated in Table 6. The resulting mixtures were kneaded for 5 minutes on kneading rolls at 180° C. and formed into sheets 0.5 mm thick. A control sheet, containing no stabilizer, was also made.

The sheets thus formed were exposed for 300 hours in a "Sunshine Weather-O-Meter" and then examined for discoloration. The results obtained are shown in Table 6.

Table 6

| Stabilizer No. | Colour |
|---|---|
| 9 | pale yellow |
| 52 | pale yellow |
| 70 | pale yellow |
| 73 | pale yellow |
| None | dark brown |

We claim:

1. A synthetic polymer composition stabilized against photo- and thermal- deterioration, wherein there is incorporated, in an amount sufficient to prevent said deterioration, a piperidine derivative having the formula

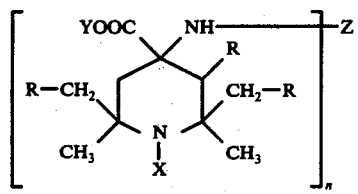

(I)

and the acid-addition salts thereof, wherein:
R represents a hydrogen atom, or an alkyl group having 1-3 carbon atoms;
X represents a hydrogen atom,
    an oxyl radical,
    an alkyl group having 1-18 carbon atoms,
    an alkenyl group having 3-6 carbon atoms,
    a 2-propynyl group,
    an alkoxyalkyl group having 1-3 carbon atoms in the alkyl moiety and 1-18 carbon atoms in the alkoxy moiety,
    a cyanoalkyl group having 2-3 carbon atoms,
    an 2,3-epoxypropyl group,
    an aliphatic acyl group having 1-12 carbon atoms,
    benzyl,
    a group of the formula —$CH_2CH(R^1)OR^2$ (wherein $R^1$ represents a hydrogen atom, a methyl group or a phenyl group, and $R^2$ represents a hydrogen atom, or an aliphatic, aromatic, aralphatic or alicyclic acyl group having up to 18 carbon atoms),
    a group of the formula —$CH_2COOR^3$ (wherein $R^3$ represents an alkyl group having 1-18 carbon atoms, an alkenyl group having 3-6 carbon atoms, a phenyl group, an aralkyl group having 7-8 carbon atoms, or a cyclohexyl group), or
    a group of the formula —$COOR^4$ (wherein $R^4$ represents an alkyl group having 1-8 carbon atoms, a benzyl group, or a phenyl group);
Y represents an alkyl group having 1-18 carbon atoms,
    an alkenyl group having 3-6 carbon atoms,
    benzyl, or
    an alkoxyalkyl group having a total of 2-4 carbon atoms;
$n = 1, 2$ or $3$; and
when $n = 1$:
Z represents a hydrogen atom,
    an alkyl group having 1-18 carbon atoms,
    an alkenyl group having 3-4 carbon atoms,
    an alkanoyl group having 2-18 carbon atoms,
    an alkenoyl group having 3-5 carbon atoms,
    a benzoyl group,
    a benzyl group,
    a phenylsulfonyl group,
    a p-tolylsulfonyl group,
    a methylcarbamoyl group, or
    a phenylcarbamoyl group optionally substituted in its phenyl moiety with a chlorine atom or with an alkyl group having 1-4 carbon atoms,
    a cinnamoyl group,
    a 3-(3,5-di-t-butyl-4-hydroxyphenyl)propionyl group,
    a phenylacetyl group,
    a phenoxyacetyl group,
    a cyclohexanecarbonyl group,
    a group of formula —$CH_2CH_2OR^5$ (wherein $R^5$ represents a hydrogen atom, or an aliphatic, aromatic, aralphatic or alicyclic acyl group having up to 18 carbon atoms),
    a group of the formula —$SO_2R^6$ (wherein $R^6$ represents an alkyl group having 1-3 carbon atoms, a phenyl group or a tolyl group),
    a group of the formula —$COOR^7$ (wherein $R^7$ represents an alkyl group having 1-8 carbon atoms or a benzyl group),
    a group of the formula —$CONR^8R^9$ (wherein $R^8$ represents a hydrogen atom or an alkyl group having 1-4 carbon atoms, and $R^9$ represents a hydrogen atom, an alkyl group having 1-18 carbon atoms, a phenyl group which may optionally be substituted, a naphthyl group, a benzyl group or a cyclohexyl group; or $R^8$ and $R^9$ jointly represent an alkylene group having 4-6 carbon atoms), or
    a group of the formula —$CSNHR^{10}$ (wherein $R^{10}$ represents an alkyl group having 1-4 carbon atoms or a phenyl group);
when $n = 2$:
Z represents an alkylene group having 1-10 carbon atoms,
    a 2-butenylene group,
    an m- or p- xylylene group,
    a carbonyl group
    a sulfinyl group,
    a sulfonyl group,
    an oxalyl group, a group of the formula —CO—R$^{11}$—CO— (wherein R$^{11}$ represents an alkylene group having 1–10 carbon atoms which may optionally be interrupted by a sulfur atom; an alkenylene group having 2–4 carbon atoms; an arylene group having 6 or 10 carbon atoms in its aryl moiety; or a cyclohexylene group), or a group of the formula —CONH—R$^{12}$—NHCO— [wherein R$^{12}$ represents an alkylene group having 2–8 carbon atoms; a phenylene group; a tolylene group; a naphthylene group; a xylylene group; a group of the formula

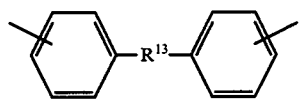

(wherein R$^{13}$ represents an oxygen atom or a methylene group), or a group of the formula

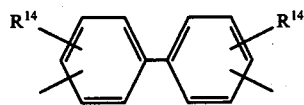

(wherein R$^{14}$ represents a hydrogen atom or a methyl group)];
when $n = 3$:
Z represents a group of formula

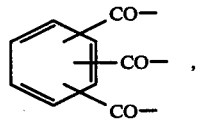

a group of the formula

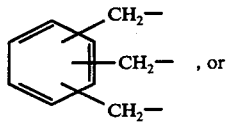, or a group of the formula

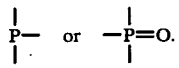

2. A synthetic polymer composition stabilized against photo- and thermal- deterioration, wherein there is incorporated, in an amount sufficient to prevent said deterioration, a piperidine derivative having the formula

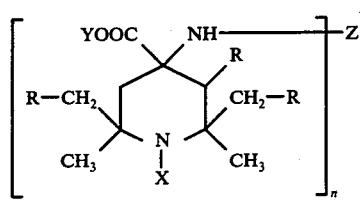 (I)

and the acid-addition salts thereof, wherein:
R represents a hydrogen atom or a methyl group;
X represents a hydrogen atom, an alkyl group having 1–4 carbon atoms, an allyl group, an alkanoyl group having 2–4 carbon atoms, an alkenoyl group having 3 or 4 carbon atoms, a 2,3-epoxypropyl group, a benzyl group, or a group of the formula —CH$_2$CH$_2$OR$^{16}$ (wherein R$^{16}$ represents a hydrogen atom, an alkanoyl group having 2–18 carbon atoms or a benzoyl group);
Y represents an alkyl group having 1–8 carbon atoms, an allyl group, a benzyl group, or an alkoxyalkyl group having a total of 3 or 4 carbon atoms;
$n = 1$ or 2; and
when $n = 1$:
Z represents an alkyl group having 1–8 carbon atoms, an alkanoyl group having 2–18 carbon atoms, an alkenoyl group having 3 or 4 carbon atoms, a benzoyl group, a benzyl group, a phenylsulfonyl group, a p-tolylsulfonyl group, a methylcarbamoyl group, or a phenylcarbamoyl group optionally substituted in its phenyl moiety with a chlorine atom or with an alkyl group having 1–4 carbon atoms;
when $n = 2$:
Z represents an alkylene group having 2–6 carbon atoms, a xylylene group, a group of the formula —CO—R$^{21}$—CO— (wherein R$^{21}$ represents an alkylene group having 2–8 carbon atoms, an alkenylene group having 2 or 3 carbon atoms, a m- or p- phenylene group, a 1,5-naphthylene group or a 1,4-cyclohexylene group), or a group of the formula —CONH—R$^{22}$—NHCO— (wherein R$^{22}$ represents a hexamethylene group, a 2,4-tolylene group, a 1,5-naphthylene group, a m- or p- xylylene group, or a methylenedi-p-phenylene group).

3. A synthetic polymer composition as claimed in claim 1 wherein said polymer is selected from the group consisting of an olefin polymer, polyamide having recurring amide groups as integral parts of the main polymer chain and polyurethane.

4. A synthetic polymer composition as claimed in claim 1, wherein:
R represents a hydrogen atom;
X represents a hydrogen atom, a methyl group, an allyl group, an acetyl group, an acryloyl group, a crotonoyl group, a 2,3-epoxypropyl group, a benzyl group, or a group of the formula —CH$_2$CH$_2$OR$^{16}$ (wherein R$^{16}$ represents a hydrogen atom, an alkanoyl group having 2–18 carbon atoms or a benzoyl group);
Y represents a methyl group, an ethyl group or an allyl group;
$n = 1$ or 2; and
when $n = 1$:
Z represents an alkanoyl group having 2–8 carbon atoms, an alkenoyl group having 3 or 4 carbon atoms, a benzoyl group, a methylcarbamoyl group or a phenylcarbamoyl group;
when $n = 2$:
Z represents a group of the formaula —CO—R$^{23}$—CO— (wherein R$^{23}$ represents an alkylene group having 2–8 carbon atoms or a p-phenylene group).

5. A synthetic polymer composition as claimed in claim 1, wherein said piperidine derivative or acid-addition salt thereof is incorporated in an amount of 0.01–5.0% by weight, based upon the amount of the synthetic polymer.

6. A compound selected from the group consisting of piperidine derivatives having the formula

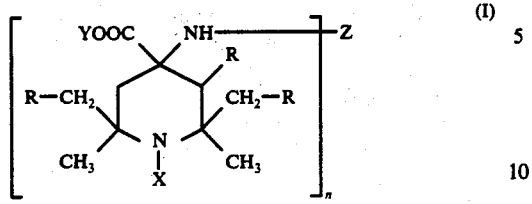

and the acid-addition salts thereof, wherein:

R represents a hydrogen atom, or an alkyl group having 1-3 carbon atoms;

X represents a hydrogen atom,
an oxyl radical,
an alkyl group having 1-18 carbon atoms,
an alkenyl group having 3-6 carbon atoms,
a 2-propynyl group,
an alkoxyalkyl group having 1-3 carbon atoms in the alkyl moiety and 1-18 carbon atoms in the alkoxy moiety,
a cyanoalkyl group having 2-3 carbon atoms,
an 2,3-epoxypropyl group,
an aliphatic acyl group having 1-12 carbon atoms, benzyl,
a group of the formula —$CH_2CH(R^1)OR^2$ (wherein $R^1$ represents a hydrogen atom, a methyl group or a phenyl group, and $R^2$ represents a hydrogen atom, or an aliphatic, aromatic, araliphatic or alicyclic acyl group having up to 18 carbon atoms), a group of the formula —$CH_2COOR^3$ (wherein $R^3$ represents an alkyl group having 1-18 carbon atoms, an alkenyl group having 3-6 carbon atoms, a phenyl group, an aralkyl group having 7-8 carbon atoms, or a cyclohexyl group) or a group of the formula —$COOR^4$ (wherein $R^4$ represents an alkyl group having 1-8 carbon atoms, a benzyl group or a phenyl group);

Y represents an alkyl group having 1-18 carbon atoms,
an alkenyl group having 3-6 carbon atoms, benzyl, or
an alkoxyalkyl group having a total of 2-4 carbon atoms;

$n$ = 1, 2 or 3; and when $n$ = 1:

Z represents a hydrogen atom,
an alkyl group having 1-18 carbon atoms,
an alkenyl group having 3-4 carbon atoms,
an alkanoyl group having 2-18 carbon atoms,
an alkenoyl group having 3-5 carbon atoms,
a benzoyl group,
a benzyl group,
a phenylsulfonyl group,
a p-tolylsulfonyl group,
a methylcarbamoyl group, or
a phenylcarbamoyl group optionally substituted in its phenyl moiety with a chlorine atom or with an alkyl group having 1-4 carbon atoms,
a cinnamoyl group,
a 3-(3,5-di-t-butyl-4-hydroxyphenyl)propionyl group,
a phenylacetyl group,
a phenoxyacetyl group,
a cyclohexanecarbonyl group,
a group of formula —$CH_2CH_2OR^5$ (wherein $R^5$ represents a hydrogen atom, or an aliphatic, aromatic, araliphatic or alicyclic acyl group having up to 18 carbon atoms),
a group of the formula —$SO_2R^6$ (wherein $R^6$ represents an alkyl group having 1-3 carbon atoms, a phenyl group or a tolyl group),
a group of the formula —$COOR^7$ (wherein $R^7$ represents an alkyl group having 1-8 carbon atoms or a benzyl group),
a group of the formula —$CONR^8R^9$ (wherein $R^8$ represents a hydrogen atom or an alkyl group having 1-4 carbon atoms, and $R^9$ represents a hydrogen atom, an alkyl group having 1-18 carbon atoms, a phenyl group which may optionally be substituted, a naphthyl group, a benzyl group or a cyclohexyl group; or $R^8$ and $R^9$ jointly represent an alkylene group having 4-6 carbon atoms), or
a group of the formula —$CSNHR^{10}$ (wherein $R^{10}$ represents an alkyl group having 1-4 carbon atoms or a phenyl group);

when $n$ = 2:

Z represents an alkylene group having 1-10 carbon atoms,
a 2-butenylene group,
an m- or p- xylylene group,
a carbonyl group
a sulfinyl group,
a sulfonyl group,
an oxalyl group,
a group of the formula —CO—$R^{11}$—CO— (wherein $R^{11}$ represents an alkylene group having 1-10 carbon atoms which may optionally be interrupted by a sulfur atom; an alkenylene group having 2-4 carbon atoms; an arylene group having 6 or 10 carbon atoms in its aryl moiety; or a cyclohexylene group), or
a group of the formula —CONH—$R^{12}$—NHCO— [wherein $R^{12}$ represents an alkylene group having 2-8 carbon atoms; a phenylene group; a tolylene group; a naphthylene group; a xylylene group; a group of the formula

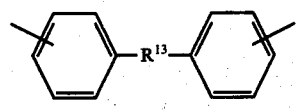

(wherein $R^{13}$ represents an oxygen atom or a methylene group), or a group of the formula

(wherein $R^{14}$ represents a hydrogen atom or a methyl group)];

when $n$ = 3:

Z represents a group of the formula

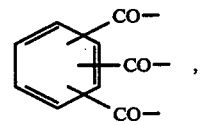

a group of the formula

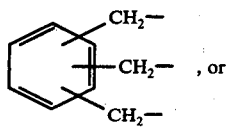

a group of the formula

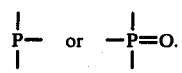

7. A compound selected from the group consisting of piperidine derivatives having the formula

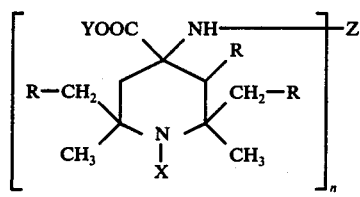

and the acid-addition salts thereof, wherein:
R represents a hydrogen atom or a methyl group;
X represents a hydrogen atom, an alkyl group having 1–4 carbon atoms, an allyl group, an alkanoyl group having 2–4 carbon atoms, an alkenoyl group having 3 or 4 carbon atoms, a 2,3-epoxypropyl group, a benzyl group, or a group of the formula —$CH_2CH_2OR^{16}$ (wherein $R^{16}$ represents a hydrogen atom, an alkanoyl group having 2–18 carbon atoms or a benzoyl group);
Y represents an alkyl group having 1–8 carbon atoms, an allyl group, a benzyl group, or an alkoxyalkyl group having a total of 3 or 4 carbon atoms;
$n = 1$ or 2; and
when $n = 1$:
Z represents an alkyl group having 1–8 carbon atoms, an alkanoyl group having 2–18 carbon atoms, an alkenoyl group having 3 or 4 carbon atoms, a benzoyl group, a benzyl group, a phenylsulfonyl group, a p-tolylsulfonyl group, a methylcarbamoyl group, or a phenylcarbamoyl group optionally substituted in its phenyl moiety with a chlorine atom or with an alkyl group having 1–4 carbon atoms;
when $n = 2$:
Z represents an alkylene group having 2–6 carbon atoms, a xylylene group, a group of the formula —CO—$R^{21}$—CO— (wherein $R^{21}$ represents an alkylene group having 2–8 carbon atoms, an alkenylene group having 2 or 3 carbon atoms, a m- or p- phenylene group, a 1,5-naphthylene group or a 1,4-cyclohexylene group), or a group of the formula —CONH—$R^{22}$—NHCO— (wherein $R^{22}$ represents a hexamethylene group, a 2,4-tolylene group, a 1,5-naphthylene group, a m- or p- xylylene group, or a methylenedi-p-phenylene group).

8. A compound as claimed in claim 6, wherein:
R represents a hydrogen atom;
X represents a hydrogen atom, a methyl group, an allyl group, an acetyl group, an acryloyl group, a crotonoyl group, a 2,3-epoxypropyl group, a benzyl group, or a group of the formula —$CH_2CH_2OR^{16}$ (wherein $R^{16}$ represents a hydrogen atom, an alkanoyl group having 2–18 carbon atoms or a benzoyl group);
Y represents a methyl group, an ethyl group or an allyl group;
$n = 1$ or 2; and
when $n = 1$:
Z represents an alkanoyl group having 2–8 carbon atoms, an alkenoyl group having 3 or 4 carbon atoms, a benzoyl group, a methylcarbamoyl group or a phenylcarbamoyl group;
when $n = 2$:
Z represents a group of the formula —CO—$R^{23}$—CO— (wherein $R^{23}$ represents an alkylene group having 2–8 carbon atoms or a p-phenylene group).

9. A compound as claimed in claim 6, selected from the group consisting of:
4-amino-4-ethoxycarbonyl-2,2,6,6-tetramethylpiperidine,
4-acetamido-4-ethoxycarbonyl-2,2,6,6-tetramethylpiperidine,
4-crotonamido-4-methoxycarbonyl-2,2,6,6-tetramethylpiperidine,
4-benzamido-4-methoxycarbonyl-2,2,6,6-tetramethylpiperidine,
4-amino-4-methoxycarbonyl-1,2,2,6,6-pentamethylpiperidine,
4-caprylamido-4-methoxycarbonyl-1,2,2,6,6-pentamethylpiperidine,
4-stearamido-4-methoxycarbonyl-1,2,2,6,6-pentamethylpiperidine, and
4-acrylamido-4-methoxycarbonyl-1,2,2,6,6-pentamethylpiperidine.

* * * * *

Disclaimer 4,118,368.—*Nobuo Soma, Syoji Morimura, Takao Yoshioka* and *Tomoyuki Kurumada*, Tokyo, Japan. SYNTHETIC POLYMER STABILIZERS. Patent dated Oct. 3, 1978. Disclaimer filed Mar. 25, 1980, by the assignee, *Sankyo Company Limited.*

Hereby enters this disclaimer to claim 6 of said patent.

[*Official Gazette, May 27, 1980.*]